(12) United States Patent
Chudy et al.

(10) Patent No.: US 7,805,217 B2
(45) Date of Patent: Sep. 28, 2010

(54) PHARMACY DISPENSING SYSTEM AND METHOD

(75) Inventors: Duane S. Chudy, Lincolnshire, IL (US); David A. Schultz, Palatine, IL (US)

(73) Assignee: AutoMed Technologies, Inc., Vernon Hills, IL (US)

(*) Notice: Subject to any disclaimer, the term of this patent is extended or adjusted under 35 U.S.C. 154(b) by 1030 days.

(21) Appl. No.: 11/003,186

(22) Filed: Dec. 3, 2004

(65) Prior Publication Data

US 2005/0125097 A1 Jun. 9, 2005

Related U.S. Application Data

(60) Provisional application No. 60/527,558, filed on Dec. 5, 2003.

(51) Int. Cl.
*G06F 17/00* (2006.01)
(52) U.S. Cl. .................. 700/237; 700/241; 700/231; 700/230
(58) Field of Classification Search .......... 700/216, 700/231–244, 213, 215, 225–227; 235/375, 235/385
See application file for complete search history.

(56) References Cited

U.S. PATENT DOCUMENTS

| | | | |
|---|---|---|---|
| 5,533,606 A * | 7/1996 | Yuyama ...................... 198/349 |
| 5,597,995 A | 1/1997 | Williams et al. |
| 5,604,692 A * | 2/1997 | Yuyama ...................... 708/714 |
| 5,610,811 A * | 3/1997 | Honda ............................ 705/2 |
| 5,648,751 A | 7/1997 | Yuyama et al. |
| 5,771,657 A * | 6/1998 | Lasher et al. ................... 53/55 |
| 5,839,257 A | 11/1998 | Soderstrom et al. |
| 5,875,434 A * | 2/1999 | Matsuoka et al. ............. 705/28 |
| 5,907,493 A | 5/1999 | Boyer et al. |
| 5,988,858 A * | 11/1999 | Yuyama et al. ............. 700/230 |
| 5,996,889 A * | 12/1999 | Fuchs et al. .................. 235/375 |
| 6,170,230 B1 * | 1/2001 | Chudy et al. ................... 53/168 |
| 6,181,979 B1 * | 1/2001 | Murakami ................... 700/216 |
| 6,195,005 B1 | 2/2001 | Maloney |
| 6,195,006 B1 | 2/2001 | Bowers et al. |
| 6,202,923 B1 | 3/2001 | Boyer et al. |
| 6,294,999 B1 | 9/2001 | Yarin et al. |
| 6,308,109 B1 * | 10/2001 | Yuyama et al. ............. 700/228 |
| 6,317,648 B1 | 11/2001 | Sleep et al. |
| 6,318,630 B1 * | 11/2001 | Coughlin et al. ............ 235/375 |
| 6,330,491 B1 | 12/2001 | Lion |
| 6,363,687 B1 | 4/2002 | Luciano et al. |

(Continued)

OTHER PUBLICATIONS

Omron Electronics LLC date unknown Electromagnetic Inductive RFID Data Carrier V700-D23P41. <www.omron.com>.

(Continued)

*Primary Examiner*—Gene Crawford
*Assistant Examiner*—Michael K Collins
(74) *Attorney, Agent, or Firm*—Foley & Lardner LLP

(57) ABSTRACT

A system for filling a prescription order for a patient includes a plurality of trays each having an RFID tag for storing a unique identifier corresponding to the prescription order, and a plurality of workstations operatively linked to one another, each workstation having an antenna for detecting the unique identifier in one of the plurality of trays, where the detecting is operative to trigger displaying a profile of at least one prescription item for the corresponding prescription order.

24 Claims, 8 Drawing Sheets

U.S. PATENT DOCUMENTS

| | | | |
|---|---|---|---|
| 6,370,841 | B1 | 4/2002 | Chudy et al. |
| 6,380,858 | B1 | 4/2002 | Yarin et al. |
| 6,415,982 | B2 | 7/2002 | Bridgelall et al. |
| 6,438,451 | B1 | 8/2002 | Lion |
| RE37,829 | E | 9/2002 | Charhut et al. |
| 6,470,234 | B1 | 10/2002 | McGrady |
| 6,483,434 | B1 | 11/2002 | UmiKer |
| 6,490,502 | B2 | 12/2002 | Fellows et al. |
| 6,496,806 | B1 | 12/2002 | Horwitz et al. |
| 6,501,379 | B2 | 12/2002 | Maloney |
| 6,520,544 | B1 | 2/2003 | Mitchell et al. |
| 6,522,945 | B2* | 2/2003 | Sleep et al. ............. 700/225 |
| 6,563,425 | B2 | 5/2003 | Nicholson et al. |
| 6,611,733 | B1* | 8/2003 | De La Huerga ............ 700/236 |
| 6,622,127 | B1 | 9/2003 | Klots et al. |
| 6,775,589 | B2* | 8/2004 | William et al. ............. 700/216 |
| 6,959,229 | B2 | 10/2005 | Eidemiller |
| 7,031,801 | B1 | 4/2006 | Hodge et al. |
| 7,070,053 | B1 | 7/2006 | Abrams et al. |
| 7,110,855 | B2* | 9/2006 | Leishman ................... 700/216 |
| 7,111,780 | B2* | 9/2006 | Broussard et al. .......... 235/381 |
| 7,118,029 | B2* | 10/2006 | Nycz et al. .................. 235/375 |
| 7,139,637 | B1* | 11/2006 | Waddington et al. ........ 700/216 |
| 7,146,247 | B2* | 12/2006 | Kirsch et al. ............... 700/236 |
| 7,155,396 | B2* | 12/2006 | Yuyama et al. ................. 705/2 |
| 2001/0002448 | A1* | 5/2001 | Wilson et al. ............... 700/233 |
| 2001/0049629 | A1 | 12/2001 | Freeman |
| 2002/0099567 | A1 | 7/2002 | Joao |
| 2002/0178074 | A1 | 11/2002 | Bloom |
| 2003/0209601 | A1 | 11/2003 | Chung |
| 2003/0233165 | A1* | 12/2003 | Hein et al. .................. 700/216 |
| 2004/0088187 | A1 | 5/2004 | Chudy et al. |
| 2005/0004700 | A1* | 1/2005 | DiMaggio ................... 700/213 |
| 2005/0055129 | A1* | 3/2005 | Chien ......................... 700/216 |
| 2006/0043177 | A1* | 3/2006 | Nycz et al. .................. 235/385 |
| 2006/0054682 | A1* | 3/2006 | de la Huerga ............... 235/375 |
| 2006/0161298 | A1* | 7/2006 | DiMaggio ................... 700/244 |
| 2008/0195247 | A1* | 8/2008 | Mallett et al. ............... 700/225 |

OTHER PUBLICATIONS

Omron Electronics LLC, date unknown, V720-Series Electromagnetic Inductive RFID System ID Tags. <www.omron.com>.

Omron Electronics LLC, date unknown, V720-Series Electromagnetic Inductive RFID System Tag Inlets. <www.omron.com>.

Statement of Understanding Regarding Certain Prior Art. Date: 1996 and 1998.

"RFID—Clever barcodes, or New Direction in Tracking?" Date: Apr./May 2003. M. Logistics. www.mlogmag.com. Pertinent Pages General background on RFIDs.

Butschli, "Firm Solves Radio-Frequency Pollution." Date: Dec. 2004. www.packworld.com. Pertinent Pages: Entire document.

McKesson Corporation. IntelliShelf-Rx brochure. Date: Copyright 2007.

McKesson Corporation. IntelliShelf-Rx press release. Date: Nov. 16, 2006.

Iverson, "Will RFID Pay off for Manufacturers?" Date: Nov. 2004. www.automationworld.com. Pertinent Pages: 10-11.

Emigh, "UPS Tests RFID with Mixed Results." Date: Feb. 28, 2005. www.eweek.com. Pertinent Page: 2.

Margulius, "The Rush to RFID." Date: Apr. 12, 2004. Infoworld. Pertinent Page: 39.

"Chipping of Goods Case Study." Chipping of Goods Secretariat, Hertfordshire, United Kingdom. Date: 2000-2002. Pertinent Pages: 2 and 4.

Margulius, "UPS Pilots an RFID Rollout." Date: Apr. 9, 2004. www.infoworld.com. Pertinent Page: 1.

"UPS Pressroom: Fact Sheet." Date: Copyright 1994-2006. www.pressroom.ups.com. Pertinent Page: 2.

Drickhamer, "Cardinal Health Releases Details of RFID Pilot Project." Date: Nov. 28, 2006. www.logisticstoday.com. Pertinent Page: 1.

Emigh, "Merger Creates $65M E-Pharmacy with RFID." Date: Aug. 25, 2004. www.eweek.com. Pertinent Page: 2.

Bone, "RFID Technology Will Protect Pharmaceutical Distribution." U.S. Pharmacist. No:29:06. Date: Jun. 15, 2004. Pertinent Pages: 1-3.

Palliparambil and Mulloy, "Thinking RFID Outside the Case." Presentation Materials. Material Handling & Logistics Conference 2005. Date: 2005. Pertinent Pages: 14-23.

SI Handling Systems, Inc. "Automated Order Selection Systems." Brochure. Date: 1984 and 1989.

AutoMed Technologies, Inc. "VersaFill System." Brochure. Date: 1996.

AutoMed Technologies, Inc. "AutoMed FDS Systems Automated Pharmacy Medication Packaging." Brochure. Date: 1998.

Automated Prescription Systems, Inc. "The Baker AutoScript II System." Brochure. Date: 1998.

Automated Prescription Systems, Inc. "Speed Accuracy and Productivity." Brochure. Date: 1998.

Automated Prescription Systems, Inc. "Pharmacy 2000." Brochure. Date: 1996.

Automated Prescription Systems, Inc. "Pharmacy 1000 Prdocuctivity That is Fast, Flexible and Affordable." Brochure. Date: 1996.

Innovation Associates, Inc. "PharmASSIST." Brochure. Date: 1998.

ScriptPro LLC. "ScriptPro Pharmacy Automation." Brochure. Date: 1996.

* cited by examiner

| CHECK ORDER FOR | |
|---|---|
| PATIENT/Rx | PICKUP TIME/MEDICATION |
| TOM GIBSON | WAITER 12:00 am TUE 28 |
| _67_ Rx 61201 | TIC TACS 15CAL<br>FASTFILL-CASSETTE#2 _62_ |
| _67_ Rx 61202 | TIC TACS WHITE 15CAL<br>QUICKFILL+C61CASSETTE#65 _62_ |
| _68_ Rx 61203 | CALTRATE 800 PLUS, 600mg<br>SHELF-3C11 _63_ |
| _67_ Rx 61204 | CERTS GREEN 5CAL<br>QP300-2 _62_ |

STOCK IMAGE TIC TACS — 318

FIG. 5

PHARMACY DISPENSING SYSTEM AND METHOD

RELATED APPLICATION

This application claims the benefit of U. S. Provisional Patent Application Ser. No. 60/527,558, filed Dec. 5, 2003, the contents of which are incorporated herein by reference.

BACKGROUND

1. Field of the Invention

The invention is directed to workflow in a pharmacy and, more particularly, to quality and process control in a personnel-driven pharmacy operation.

2. Background of the Invention

Pharmacies are an important source of medications and health-related products for a wide range of people including, for example, retail customers, mail-order customers, hospitalized patients and residents of alternate site (e.g., long term care) facilities. A pharmacy serving the needs of such people may be located, for example, in a retail environment such as a drugstore, or in a location adjunct to the hospital or alternate site facility. A typical pharmacy is staffed by at least one registered pharmacist and may be further staffed by trained pharmacy technicians and clerks.

Pharmacy personnel provide a broad range of services and information. For example, the pharmacist typically has overall responsibility for ensuring that all prescription orders for medications and health-related products are filled properly. The pharmacy technicians may assist the pharmacist in filling of the prescription orders and in replenishment of the medication inventory. Pharmacists and pharmacy technicians commonly provide other important services such as interaction with customers, doctors and care givers, a providing of health-related advice, data entry, and a processing of medical and financial information associated with a filling of the prescription orders. Providing advice and information may include direct interaction with others, while data processing and order filling typically involve interaction between the pharmacy personnel and a computer or with the medications and products needed to fill the prescription orders. For example, filling of the prescription orders may involve locating one or more medications or products at a static storage shelf or other storage location, dispensing a quantity of the medications or products required to fill each prescription in an order, manually packaging the medications in containers (such as bottles and vials), and dispensing the packaged medications and products to the customer, doctor, or care giver. As used herein, the term "patient" refers to any person or persons for whom a prescription order is filled.

It is highly desirable for the pharmacist and pharmacy technician to be available for providing value added services, such as by providing health-related advice and information to customers, doctors and care givers. It is also desirable to fill each prescription order at a lowest possible cost, as explained for example in co-pending application Ser. No. 10/283,529, herein incorporated by reference. Such cost function may be defined in terms of many variables, such as the total time required to fill each prescription order, the spacial distance traveled by the pharmacy personnel within the pharmacy in order to fill each prescription order, and the cost to the pharmacy of the medication and products used to fill each prescription order. The cost function may also be constructed in order to obtain cost reduction through coordination of the filling of co-pending prescription orders.

Additional desired characteristics of a pharmacy include a need for accuracy and the elimination of errors in the filling of prescription orders.

Accordingly, there has been a growing use and acceptance of automation in connection with filling of prescription orders by pharmacies. Such automation can include the use of computerized information databases for processing medical and financial information, the use of automated apparatus for dispensing medications and articles, and the use of machine-readable code (e.g., bar coding) for purposes of ensuring accuracy in filling of the prescription orders and in maintaining inventory control. An improvement in pharmacy efficiency results in a better overall level of service to the customer, doctor or care giver.

Despite benefits resulting from a use of automation in the pharmacy environment, there is generally a need for human beings as participants in the prescription order filling process. Pharmacy personnel are required to make many complex decisions and many tasks may be performed more efficiently in a manual manner. In addition, judgments must be made, for example, as to the medications and products best suited to the customer's needs. It may be necessary to determine the most efficient path for locating, obtaining, packaging, and dispensing individual components of a prescription order, in a manner that minimizes a potential for error.

It is therefore desirable to implement systems that eliminate risks of error while improving efficiency. It is also desirable to improve logistics and quality control in a human-assisted prescription order filling process within the pharmacy.

OBJECTS OF THE INVENTION

It is an object of the invention to provide an improved system and method of filling prescription orders overcoming some of the problems and shortcomings of the prior art, including those referred to above.

Another object of the invention is to provide a system and method of filling prescription orders providing traceability of individual order filling operations.

Another object of the invention is to provide an automated pharmacy system having a small footprint.

Still another object of the invention is to provide a system and method of filling prescription orders that automatically organizes operations of various pharmacy storage locations by their proximity to a receptacle.

Yet another object of the invention is to provide a scalable level of automation for a prescription filling operation in a pharmacy.

Another object of the invention is to provide an integrated modular system and method of filling prescription orders where partitioning of a prescription order for filling is triggered by a portable receptacle.

How these and other objects are accomplished will become apparent from the following descriptions and drawing figures.

SUMMARY OF THE INVENTION

According to an aspect of the invention, a system for filling a prescription order for a patient includes a plurality of trays each having a radio frequency identification (RFID) tag, a tray programmer structured for programming a unique identifier into the RFID tag of one of the plurality of trays, the unique identifier being associated with the prescription order, and a plurality of workstations operatively linked to one another, each workstation having an antenna for detecting the unique identifier, and automatically displaying a profile of medication for the prescription order.

According to another aspect of the invention, a system for filling a prescription order for a patient includes a plurality of trays each having an RFID tag for storing a unique identifier corresponding to the prescription order, and a plurality of workstations operatively linked to one another, each workstation having an antenna for detecting the unique identifier in one of the plurality of trays, where the detecting is operative to trigger displaying a profile of at least one prescription item for the corresponding prescription order.

According to a further aspect of the invention, a system includes a tray having an RFID tag containing a unique identifier, a plurality of automated medication dispensing machines each structured for dispensing individual medication amounts, and a workstation adapted for receiving the tray and reading the unique identifier, and having a memory for storing information of a prescription order, where the workstation is structured so that when the unique identifier read by the workstation is associated with the prescription order, the workstation accesses the information of the prescription order and readies an individual prescription item for dispensing by one of the medication dispensing machines.

According to a still further aspect of the invention, a method of filling a prescription order includes entering a prescription order, associating the prescription order with an RFID identifier of a tray, detecting the RFID identifier when the tray is placed proximate a human-assisted prescription order filling station, and displaying items of the prescription order at the human-assisted prescription order filling workstation.

According to another aspect of the invention, a method includes providing a tray having an RFID tag containing a unique identifier, providing a plurality of automated medication dispensing machines each structured for dispensing individual medication amounts, and providing at least one workstation adapted for receiving the tray and reading the unique identifier, and adapted for retrieving information of a prescription order, where the workstation is structured so that when the unique identifier read by the workstation is associated with the prescription order, the workstation accesses the information of the prescription order and readies an individual prescription item for dispensing by one of the medication dispensing machines.

According to another aspect of the invention, a method includes providing a plurality of trays each having an RFID tag for storing a unique identifier corresponding to the prescription order, and providing a plurality of workstations operatively linked to one another, each workstation having an antenna for detecting the unique identifier in one of the plurality of trays, where the detecting is operative to trigger displaying a profile of at least one prescription item for the corresponding prescription order.

According to yet another aspect of the invention, a method includes providing a plurality of trays each having an RFID tag, providing a tray programmer structured for programming a unique identifier into the RFID tag of one of the plurality of trays, the unique identifier being associated with the prescription order, and providing a plurality of workstations operatively linked to one another, each workstation having an antenna for detecting the unique identifier, and each being structured for automatically displaying a profile of medication for the prescription order.

As a result of implementing the invention, paperwork associated with filling prescription orders is reduced or eliminated. Workflow is fully adaptable to a technician's choice of which workstation of a plurality of workstations she wishes to proceed to next, thereby providing adaptation to changing circumstances such as a temporary bottleneck at a given location. A scalable pharmacy design is accommodated for implementing automation and high levels of quality assurance while maintaining a human-assisted control of pharmacy operations.

BRIEF DESCRIPTION OF THE DRAWINGS

FIG. 5 is a display screen showing information regarding multiple individual prescription items of a prescription order being filled according to an exemplary embodiment of the invention.

DETAILED DESCRIPTION OF PREFERRED EMBODIMENTS

Figure 1:
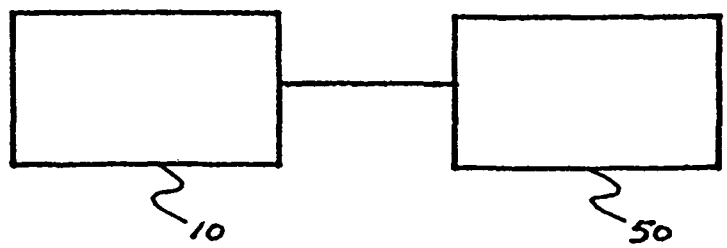
FIG. 1 is a highly schematic view of a prescription order fulfillment system according to an exemplary embodiment of the invention.
Figure 2:
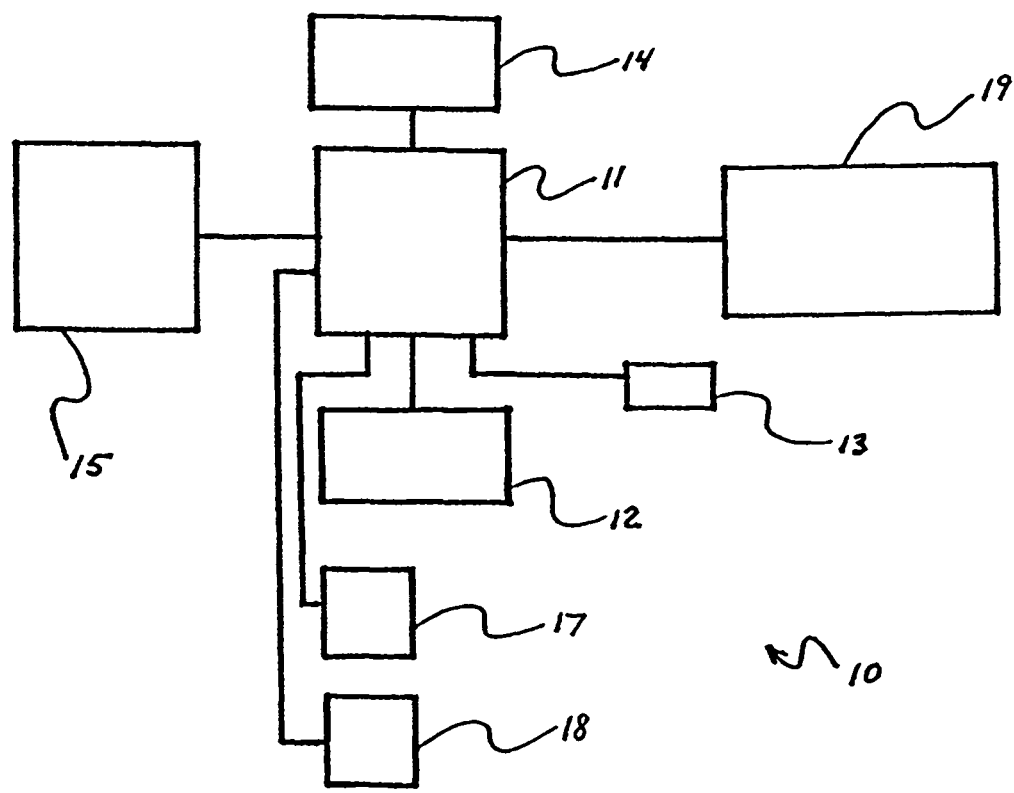
FIG. 2 is a highly schematic view of a workstation that may be used in the system of FIG. 1.

FIGS. 1-2 show a prescription order fulfillment system 1 according to an exemplary embodiment of the invention. A workstation 10 obtains order entry information from an order entry location 50. The structure and orientation of order entry location 50 may vary and may comprise any number of alternate sources of prescription information. For example, the order entry location 50 may be at a same location as the workstation 10, so that a process of order filling may be performed at the same site as a process of obtaining the prescription order. Accordingly, an order entry technician may also perform the duties of a pharmacy technician, or work from the same workstation.

Another example of an order entry location 50 is a dedicated computer terminal at which an order entry technician receives a paper prescription from a patient, nurse, etc. The paper prescription contains information regarding individual prescription items of the prescription order. The order entry technician enters the prescription order information and related information, such as that regarding insurance, method of payment, etc. An adjudication of the prescription order may be performed at the order entry location 50 in cooperation with a pharmacy information system (PIS). A properly adjudicated prescription order is then released by the PIS to a database, such as a database cooperating with a central computer. Queueing and associated functions of order filling may be implemented using such a system. Additional control may be provided by designating particular workstations for receipt of prescription order information from the database.

Another variation of an order entry configuration includes an interface between the workstation 10 and a telephone network (not shown), so that a nurse at a doctor's office, a doctor, or a patient is able to phone in her prescription order via a known automated system.

Figure 8A:
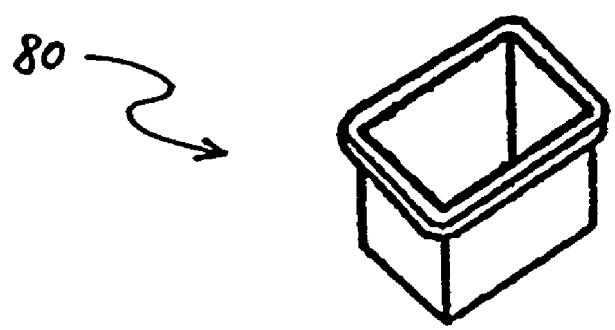
FIG. 8A shows a three-dimensional view of a tray.
Figure 8B:
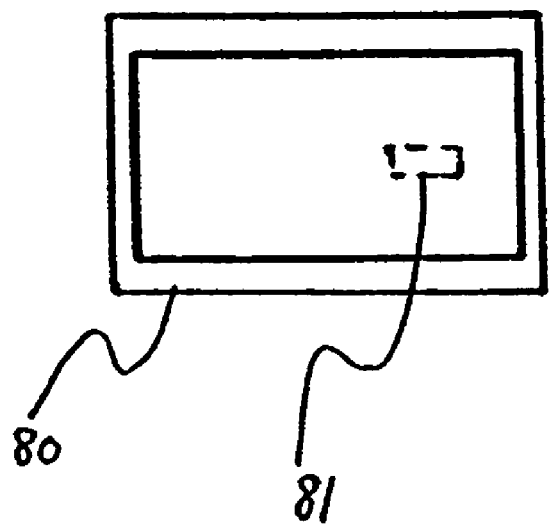
FIG. 8B shows a top view of the tray of FIG. 8A, according to an exemplary embodiment of the invention.

A given workstation 10 has a computer 11 with a number of standard input and/or output devices including a keyboard 12, a mouse 13, and a display 14. The display 14 may be either a touchscreen or non-touchscreen type. In addition, the workstation 10 includes an RFID reader 15 for reading a unique identifier in an RFID tag 81 located in a tray 80 (see, e.g., FIGS. 8A-B). RFID reader 15 is able to read and/or write data from/to RFID tag 81 without contacting RFID tag 81.

By placing the RFID tag 81 within tray 80, RFID tag 81 is resistant to damage from dirt, water, abrasion, chemicals, reflected lights, etc. The size of the RFID tag 81 may be very small and have a thin shape since RFID tag 81 does not require a battery. For example, electric power may be transmitted by electromagnetic induction from a flat read/write antenna element in RFID reader 15 to RFID tag 81. RFID tag 81 may be an inductive, capacitive, or other RFID type, and the cost of RFID tag 81 is preferably minimized since the requirements for RFID tag 81 may be minimal compared with some RFID applications. For example, an RFID tag generally contains integrated non-volatile memory that allows data to be written to and read from individual tags, but a system and method of the invention does not require user programming of RFID tag 81, and RFID tag 81 may be factory programmed with a unique identification number so that the tray 80 may be uniquely identified. Therefore, the RFID reader 15 need not program RFID tag 81, and RFID tag 81 need not be reprogrammable. RFID tag 81 has a memory of 44 bytes, 96 bytes, 128 bytes, or other similar size, being large enough to provide trillions of possible unique identifiers. Accordingly, if desired for a particular application, trays 80 may be recycled by reprogramming that always uses a new unique identifier. For example, security reasons and accounting software may dictate that a new number be assigned for each new prescription order.

RFID reader 15 preferably has a flat upper surface adapted for securely holding a tray 80 while a prescription order is being filled. The face of the read antenna of RFID reader 15 is preferably disposed in parallel with such upper surface, and the face of the antenna of RFID tag 81 is also disposed in parallel with the upper surface when tray 80 is placed on RFID reader 15. The communication range for reading an RFID tag 81 is designed to prevent detection of the RFID tag 81 at any time other than when tray 80 is in the reading position on RFID reader 15. By controlling the communication range, premature or unintended detections are prevented. Suitable read/write antenna elements and RFID tags 81 are available from Omron. A system 1 may include such a controller for interfacing computer 11 with the antenna of RFID reader 15. Such a controller is also available from Omron.

Figure 3:
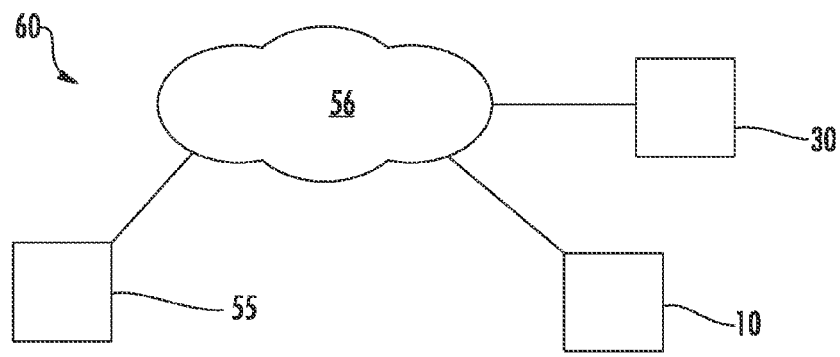
FIG. 3 is a highly schematic view of a computer network used in an exemplary embodiment of the invention.

FIG. 3 shows an exemplary computer network 60 used for implementing a system according to the invention. Various workstations 10, 30, and central computer 55 may be configured respectively as clients and server in a known manner. For example, workstations 10, 30 may obtain prescription information as clients connected to central server computer 55. A small workgroup network (e.g., Ethernet) having standard cabling between computers may be used. Any suitable computer networking system 56 such as a LAN or WAN may be implemented for exchanging prescription order and other related information such as insurance, billing, inventory, etc. between computers (e.g., including a use of the PIS). Various devices such as printers, automated dispensing machines, barcode readers, order entry terminals, checkout registers, telephone networks, other local or wide area networks, and other equipment may also be a part of computer network 60. In a simple form, one or more trays 80 indicate a patient's prescription order, so that a workstation 10, 30 reading the RFID information of a tray 80 only needs to associate the RFID information with the prescription order by accessing the database of the central computer 55.

Figure 4:
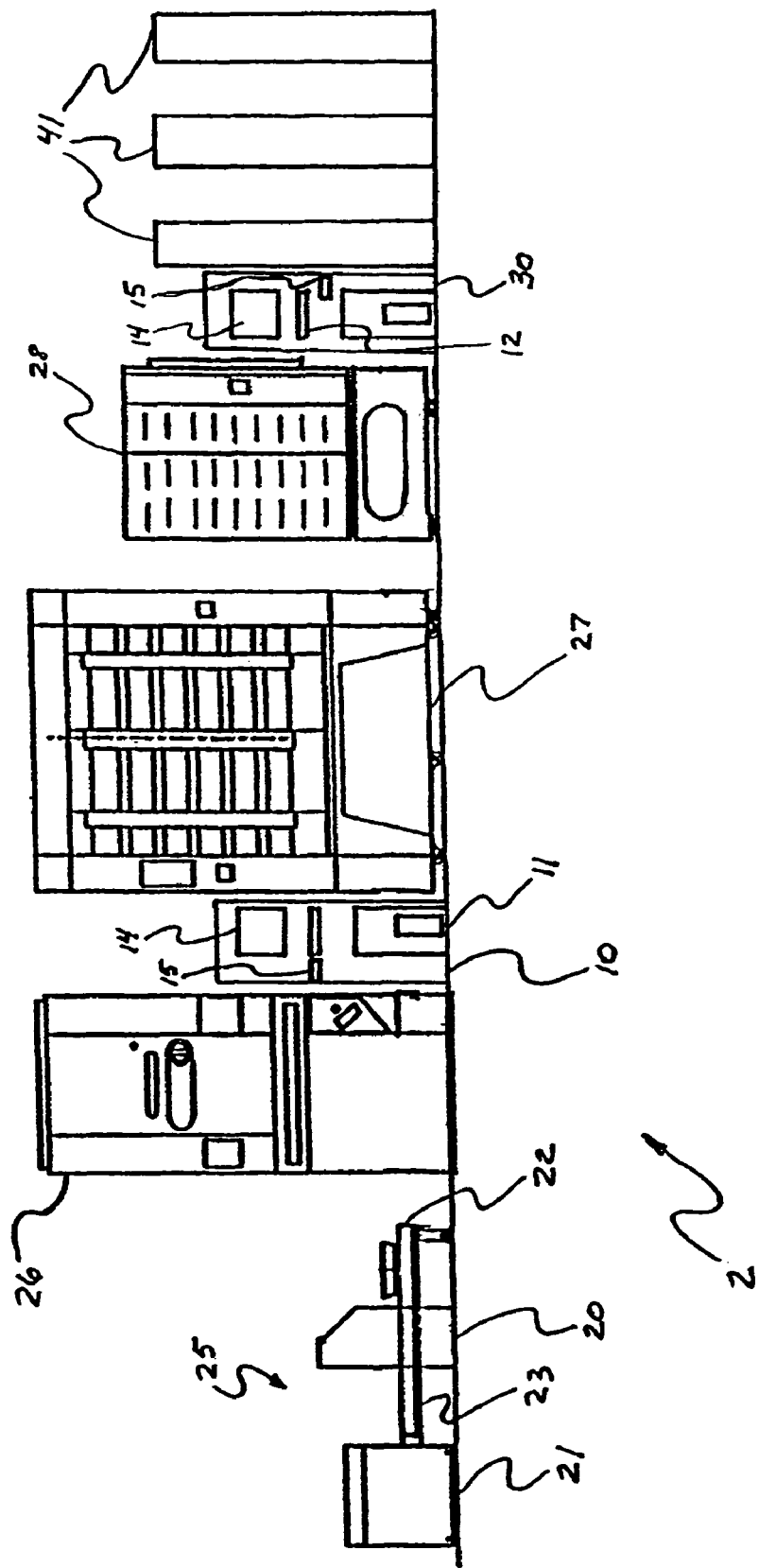
FIG. 4 shows an exemplary embodiment of a multiple workstation system application of the invention.

An exemplary multiple workstation pharmacy 2 is shown in FIG. 4. A pharmacy or other prescription fulfillment center may have a tray programmer 25 that communicates with central computer 55 and/or a workstation 10, 30 for initiating the filling process for a prescription order. Tray programmer 25 may include a tray feed station 21, a conveyor transport mechanism 23, an RFID programmer 20, and an output station 22. An exemplary tray feed station is disclosed, for example, in U.S. Pat. No. 6,370,841 granted to Chudy, et al., herein incorporated by reference. Tray programmer 25 adds RFID programmer 20 along with associated control systems.

When the filling of a prescription order is initiated, the prescription order is associated with a unique identifier and the identifier is programmed by the tray programmer 25 into RFID tag 81 in a tray 80. For example, central computer 55 assigns unique numbers and then programs the trays 80, or tray programmer 25 reads a pre-programmed unique identifier of a tray 80 being fed to output station 22 and central computer 55 associates this read number with a prescription order being initiated. An order filler such as a pharmacy technician retrieves the associated tray 80 from output station 22 and carries the tray 80 to a first workstation 10.

Workstations 10, 30 may be used at intervals in a pharmacy as order-filling stations, the intervals being designed so that work flow achieves a desired goal such as efficiency, optimum use of floorspace, maximum throughput, adapting to a particular configuration of storage locations, etc. For example, workstation 10 is located proximate tablet dispensing station 26 and ampule dispensing station 27. When the technician places tray 80 on RFID reader 15, individual items of the associated prescription order are displayed on touchscreen 14 of workstation 10. The prescription items in the area proximate workstation 10 may be highlighted on display screen 61 of touchscreen 14. The technician may press a graphical user interface (GUI) icon on touchscreen 14, which activates the corresponding automated dispenser 26, 27, or other, causing the dispenser 26, 27, or other to proceed to fill the selected prescription item. A selection of a particular item of the prescription order activates a display of an image 318 of the individual prescription item. When tray 80 is placed on RFID reader 15, the display screen 61 may include images 318 for any and/or all of the individual prescription items of a prescription order. In addition, pressing a GUI icon 62 may place information regarding filling the respective prescription item into a queue.

Figure 9:
FIG. 9 shows a checksheet that may be printed and/or displayed for all or part of a prescription order, according to an exemplary embodiment of the invention.

The '529 Application cited above details a WorkPath (™) software that may be adapted for use with the present system 1, 2, such as in a client-server architecture. Workstations 10, 30 may include a label printer 17 (e.g., FIG. 2) that automatically prints a label, when required, for a prescription item being filled, the particular automated dispensing machine 19 may have its own internal label printer (not shown), the prescription item may have its label already attached, or the particular label may be printed at a stand-alone printer (not shown) for attachment to the prescription item at a separate location. In addition, WorkPath has a checksheet function, whereby a checksheet 269 (FIG. 9) showing a filling sequence in which the individual prescription items 307 of a prescription order 305 are to be fulfilled may be displayed and/or printed for all or part of a prescription order 305. The checksheet 269 may include displaying images 318 for any or all of the listed prescription items 307, and may include the name 301 of a patient, a prescription number 309, a quantity 316, special instructions 273, barcode(s) 271, descriptive text information 311, storage location information 313, storage location icon 315, and other information.

Figure 6:
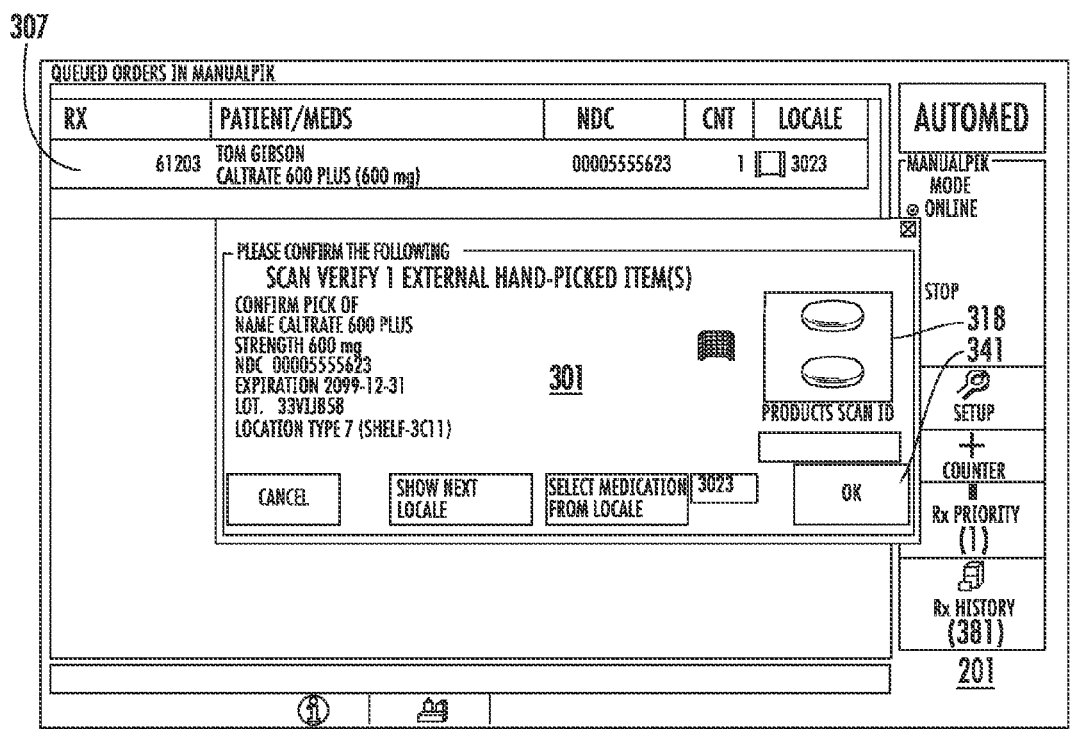
FIG. 6 is a display screen showing information regarding an individual prescription item being manually filled from a predetermined shelf location according to an exemplary embodiment of the invention.

When all the prescription items for the prescription order to be filled by tablet dispensing station 26 and by ampule dispensing station 27 have been processed, the technician picks up tray 80, proceeds to workstation 30, and places tray 80 onto RFID reader 15 of workstation 30. Upon placing tray 80 onto RFID reader 15, the prescription items to be filled from storage locations proximate workstation 30 are displayed on touchscreen 14 of workstation 30. In this example, workstation 30 is proximate automatic unit-of-use article dispenser 28 and storage shelves 41. When the technician presses a GUI icon 62 corresponding to a prescription item to be filled from unit-of-use dispenser 28, the prescription item is automatically filled. When the prescription item selected by the technician is located on a storage shelf 41, the touchscreen display screen 201 indicates the exact shelf location where a quantity of the respective prescription item may be found, as shown in FIG. 6. The technician may activate a printing of a corresponding label for the prescription item by touching a separate icon on the touchscreen 14, or the workstation 30 may automatically print such label when the corresponding prescription item is selected on the touchscreen 14.

When a given prescription order has been filled, the technician places the filled tray 80 onto a nurse's cart, onto a will-call shelf location, or in an other filled prescription area. Alternatively, the technician may place tray 80 onto an intermediate shelf (not shown), such as when she has partially filled a prescription order and desires to take a lunch break and fill the remainder of the prescription order at a later time. The intermediate shelf may also be used when a particular prescription item of a prescription order is back-ordered and the prescription order remains incomplete. Similarly, since the tray 80 automatically activates a display of the individual items in a prescription order whenever the tray 80 is placed onto an RFID reader 15, the technician may fill the order in any manner she deems appropriate, such as by first proceeding to a remote workstation if a nearby workstation is busy. The sequence of filling is independent of the movement of tray 80 so that, for example, in an emergency, a partially-filled tray 80 may be placed aside while the emergency (e.g., STAT) prescription order is being filled. When tray 80 resumes the process of being filled, a placement of tray 80 onto an RFID reader 15 at a workstation displays any remaining unfilled prescription items of the order.

FIG. 5 shows an exemplary touchscreen display 61 having a list 67, 68 of prescription items to be filled at a given workstation. In this example, the display screen 61 contains GUI icon 62 representing a storage location that is in an automated dispensing machine. A manual type GUI icon 63 represents that the respective prescription item is at a particular shelf location. When the technician presses her finger on GUI icon 63, a label is automatically printed for the prescription item and, as shown in FIG. 6, screen display 201 is provided with a popup box 301 requesting that the technician scan verify the filled prescription item by scanning the label with a barcode reader 18 and by visually comparing the displayed image 318 of a representative pill with the contents of the filled vial.

Any number of automated medication dispensing machines may be used in conjunction with a workstation 10, 30, including but not limited to dispensers of oral solids, units-of-use, injectables, IVs, ampules, vials, syringes, etc. The form of an automated dispensing machine may include a vending, cassette, vibration feed, roll packetizing, robotic, conveyor feed, automated line filling, and/or other type of automated machine. Shelving and machines may be semi-automated, such as by using a carousel or similar rotating storage and retrieval structure where access to a prescription item storage location is simplified and/or storage capacity is increased. Individual workstations 10, 30 communicate with the various devices to send them commands or receive status, such as by a hard-wired serial interface. Any suitable interface between workstations 10, 30 and automated dispensing machines may be used, including wireless, RS 232/485, USB, etc. Programs in workstations 10, 30 update a central database on central computer 55 (e.g., server). The database is accessed by all client computers and the server to communicate progress of the prescription order from entry to checking and filling. In addition, a wireless handheld computer (not shown) may be used for tracking replenishment of storage locations, for locating stock in the drawers and shelves, etc. The information exchanged with automated dispensing machines may differ according to a number of processes being performed by the particular machine. At a minimum, the serial information transmitted to automated dispensing machines includes the location of the particular medication and the quantity. Additional serial communication information between a workstation 10, 30 and an automated dispensing machine 19 may be required for implementing processes such as label printing, sequencing of roll packetizing, refrigeration of compartments in a dispenser, etc.

In addition, a tote transfer conveyor system (not shown) may be used to accommodate a particular site's requirements. In such a system, a number of conveyors may be placed end-to-end to move trays/totes from one station to another. Such a system may include corner conveyors that facilitate a change in direction (e.g., ninety degree turn in tote direction), straight conveyors, conveyor tote elevator(s) that change a position of a given tote from a floor level conveyor for automated machine dispensing to a raised level for manual pick and filling operations. Such a system may also include a conveyor queue tower that receives totes/trays, for example, from the conveyor tote elevator and retains them for a subsequent checking or bagging process, or for queueing during a sequenced or similar order filling process. An example of such a system is the AUTOFILL system, available from AutoMed Technologies, Inc., of Vernon Hills, Ill.

It is noted that a large prescription order may be assigned to more than one tray 80. In such a case, each tray 80 may be assigned to specific items of the prescription order. A multiple position RFID reader (not shown) may be used at a final quality control station for determining whether all of the individual prescription items for the prescription order are present in the multiple trays 80. Different colored trays 80 may be used, for example to differentiate a STAT order, an order for a particular nursing cart, an order for a particular destination, etc. Workstation 10, 30 may include a printer 17 adapted for printing a checksheet along with labels for identifying the particular patient corresponding to the prescription order. Such a checksheet and labels may be placed in the tray 80, and may be in the form of a printed bag into which all or some of the individual prescription items of an order may be placed. In addition, workstations 10, 30 may be used at any time by a pharmacy technician, nurse, doctor, pharmacist, etc. for checking a filled tray for accuracy, for example, prior to releasing the prescription order to a patient, nursing cart, etc.

Figure 7A:
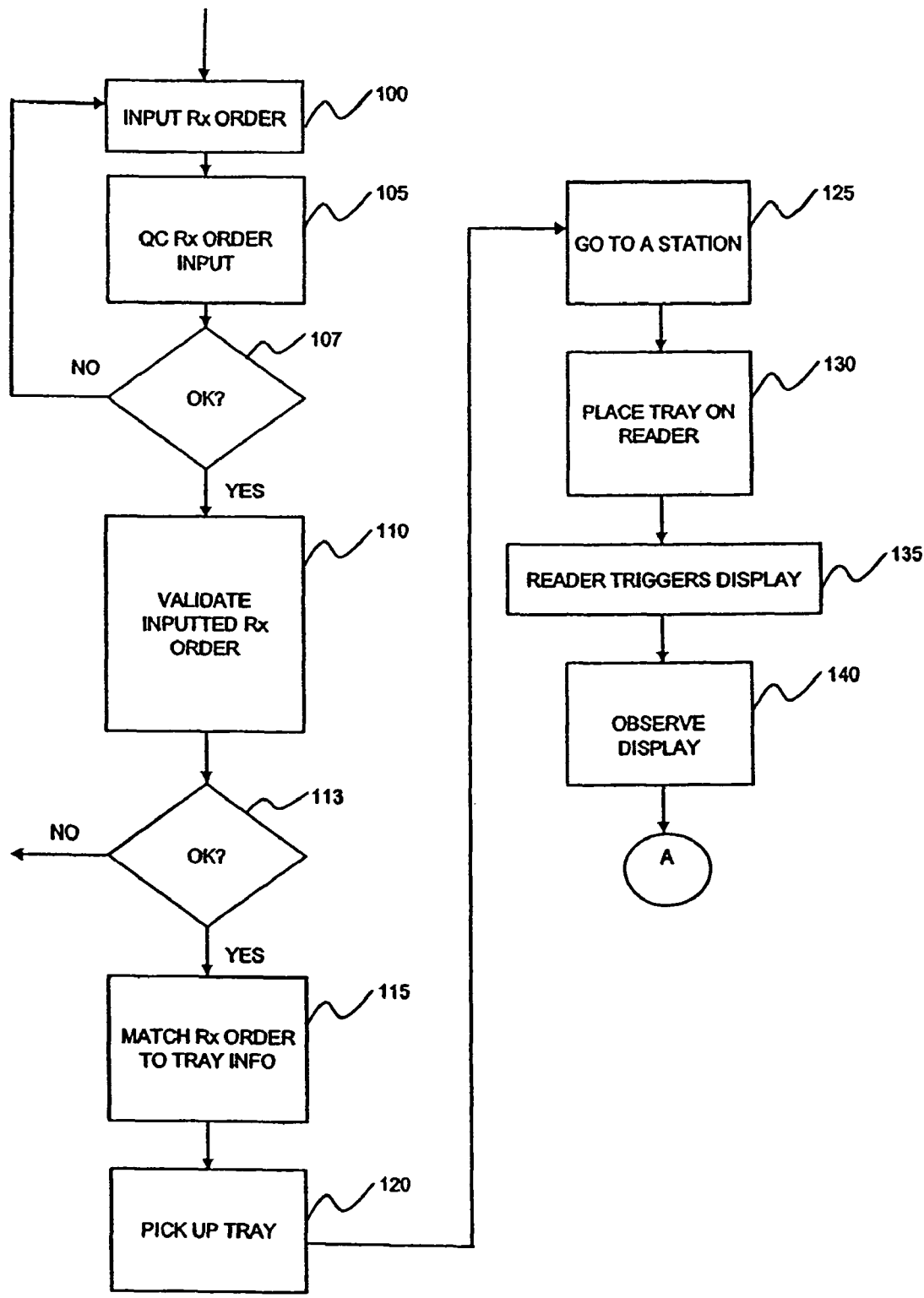
FIGS. 7A-B show a flowchart for describing a method according to an exemplary embodiment of the invention.
Figure 7B:
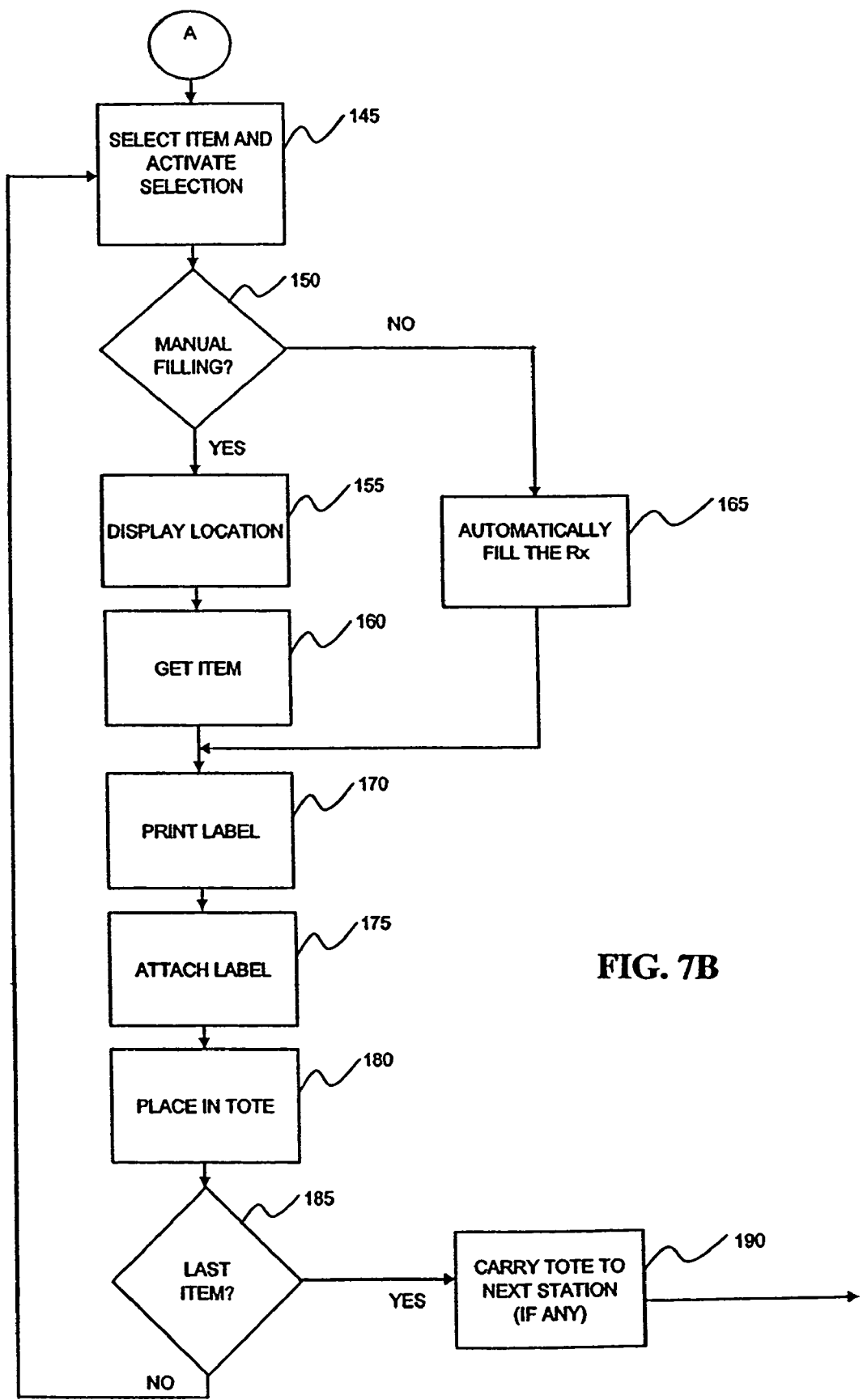

An exemplary prescription order filling process is now described with reference to FIGS. 7A-B. At step 100, a prescription order is input to a computer. For example, a patient takes her prescription to a pharmacy and hands the prescription to a pharmacy technician and the technician types the individual prescription information on a computer keyboard. The prescription information becomes an order entry in a database (e.g., PIS) that is in communication with an order entry computer, either locally or at a remote location. The order entry may be obtained by the database in a variety of ways. For example, a group of one or more individual prescription orders may be transferred between locations using intranets, internets, the Internet, etc.

At step 105 the order entry is checked for accuracy, such as by the order entry technician or by the pharmacy technician who retrieves the order. Many methods may be concurrently implemented for checking order accuracy, including but not limited to use of charts such as computer algorithms that match a profile of the patient with a dosage, type of medication, quantity, interaction information, etc., algorithms that perform spell checking or similar evaluation of entered text, etc. In step 107, when it is determined that order entry has been performed correctly, the prescription order may be forwarded to a database for subsequent retrieval and processing. If it is determined that the order has been incorrectly entered, the order is kicked back to an order entry station for re-entry or correction. An example of step 107 is a spell checker.

When a prescription order is retrieved by a pharmacy technician at step 110, she validates the prescription order, for example, by telephoning the doctor's office indicated on the prescription slip, by accessing validation information from a central computer such as by retrieving a patient's date of birth, mother's maiden name, or other personal information. Adjudication and validation of the prescription order may include a use of a PIS, and may include a combination of automated and manual processes, including obtaining a release of the prescription order from a PIS, placing prescription order information in a queue, etc. The technician may ask the patient to validate/verify such personal information or provide health insurance information. At step 113, when it is determined that the prescription order has been validated, the technician proceeds to fill the order. If the prescription order is not able to be validated, the technician may put the prescription order on hold pending receipt of the validation, or may cancel the order for processing until the order is able to be validated. The processes of order entry, order retrieval, and validation may be combined or kept separate depending on a particular application.

At step 115, the technician matches a chosen validated prescription order to a tray. She may activate a tray programmer or assigner to do such matching, for example by assigning a unique identifier contained in an RFID tag located in the tray to the chosen prescription order. The unique identifier may be programmed into the RFID tag at the time the technician selects the particular prescription order for fulfillment, by activating a programmer to enter a new unique identifier into a tray. Such a tray programmer may automatically dispense the tray to a separate location for order filling, or the tray programmer may be proximate the technician's workstation. Alternatively, the pharmacy technician may first retrieve a prescription order, then pick up a new tray from a stack, place the tray onto an RFID reader, and assign a unique identifier that is preloaded in the tray to the prescription order on her display screen.

At step 120, the technician picks up the tray and proceeds to a prescription filling workstation 10 at step 125. Workstation 10 may be connected to automated dispensing machines, it may be a workstation in a pharmacy location proximate shelves and other storage locations, or workstation 10 may be intended to service both a manual filling of prescription items from shelves as well as automatically filling prescription items by use of automated dispensers. At step 130, the technician places the tray onto a tray reader located at the chosen workstation. The tray reader detects the unique identifier in the RFID tag and presents information concerning this unique identifier to a retrieve_order routine running on the workstation. The retrieve_order routine formats this information into a request for order information. The request for order information is then presented to the database manager for retrieving the stored order information from the database. The request for order information may be included in a data stream over a network, either via a locally managed operating system or via an engine cooperating with a standard system configuration such as UNIX. The database may in fact reside locally in the workstation, as a result of the workstation being connected with the order entry device, by the workstation previously receiving a batch of orders, and by other methods. The request for order information may alternatively be transmitted via a wireless communication path, processed in a batch manner, or may be communicated by any suitable process and structure to a database manager.

At step 135, the workstation receives the requested order information from the database manager and processes the order information for displaying the information to the technician on a display device connected to the workstation. FIG. 5 shows an exemplary order screen display 61. At step 140, the technician views the displayed order screen 61 and determines which individual prescription items she wants to fill next. The technician may, at step 145, select order items and may initiate processes by, for example, pressing her finger against a graphical user interface (GUI) symbol located on a touchscreen display, by positioning a pointer on a screen symbol and then click-selecting the screen symbol, by entering keystrokes on a keyboard, by voice activation, etc. The GUI symbol may represent a location where an individual prescription item is located. For example, the GUI may represent an automatic unit-of-use dispensing machine, an automatic oral solids dispensing machine, an automatic ampule dispensing machine, an automated medication packetizing machine, a storage shelf location, or any other location for the particular selected individual prescription item.

At step 150, the technician determines whether the selected prescription is located at a storage location requiring manual retrieval or at an automated storage location. When the selected prescription item is at a shelf location requiring manual retrieval, the display at step 155 indicates the shelf number and shelf location of the item so that the technician may proceed directly to the item in step 160. Preferably, the shelves are located in an area where the desired medication may be easily obtained from a bulk container, counted, and packaged while reducing the risk of spillage or other mishap. The shelved prescription item may alternatively be pre-packaged in convenient quantities such as in quantities favored by doctors when writing the prescription orders. When the selected prescription item is located at an automated location, the workstation at step 165 communicates information regarding the prescription item to the automated dispensing machine for subsequent automated filling of the prescription item. The workstation translates information concerning the desired item into machine language for communication to the given automated dispensing machine. The automated dispensing machine receives the machine code and dispenses the prescription item, either directly into the tray or to a convenient location for retrieval by the technician.

At step 170, a label is printed for the prescription item. The automated dispensing machine may have a self-contained label printer structured for formatting information concerning a prescription item being filled and then printing such information on a label to be affixed to a vial or other container for holding the medication or related prescription item. The automated dispensing machine may apply the label to the vial automatically, may separately dispense the label, may communicate print machine code to an external printer, etc. A label for the selected prescription may be separately printed by the technician selecting a label_print routine at the workstation. The label_print routine may be integrated into a workstation algorithm, for example, associated with a selection of a next item. The printed label may be manually or automatically placed onto a container, such as a vial. It may be desirable to add redundancy to quality assurance procedures such as by preventing the selection, filling, or label printing of a subsequent prescription item until a label has been removed from a printer, until a label has been attached to a vial, scanned by a barcode reader, and verified, until a handshaking signal is received from an automated dispensing machine, etc.

The label information may include a text description of the prescription item, the quantity information, a barcode, an address and phone number of the pharmacy, doctor information, patient information, a graphic showing the particular tablet, capsule, or other form of the particular medication, etc. The label information may be displayed on the display device of the workstation so that the technician may verify that the prescription item on the screen matches an actual filled item in her hand or in the tray. Alternatively, the technician may pass the affixed label across a barcode reader connected to the workstation. The barcode information thereby obtained is then automatically compared with the items of the particular prescription order to verify that the information matches a previously selected item. When the technician is satisfied that the selected prescription item has been filled correctly, she places the filled prescription item into the tray at step 180.

At step 185, it is determined whether the filled prescription item is the last item of the prescription order to be filled at the present workstation. If not, the technician proceeds to step 145 and repeats the order filling process by selecting a next prescription item on the workstation display. If the just-filled prescription item is the last prescription item to be filled at the present workstation, the screen may indicate a next workstation or other location for subsequent placement of the tray containing filled prescription items. The display may indicate a next workstation based on efficiency and reduction of cost, proximity, availability, etc. determined by an efficiency routine in software. At step 190, the technician carries the tray to another workstation and places the tray onto the RFID reader of the new workstation, whereupon the reader detects the unique identifier of the RFID tag of the tray and displays a list of prescription items to be filled at that workstation. Subsequently, the technician performs filling of additional prescription items at the new workstation, in a manner as just described beginning at step 125.

As noted above, a person desiring to perform additional quality control or checking of the contents of a tray 80 may pick up the tray 80 and place it on an RFID reader 15 of a given workstation 10, 30. A system may include a separate workstation dedicated to checking and verification of prescription orders, for example prior to packing and shipping, at a nursing station, etc. When the person places the tray 80 onto the RFID reader 15, a list of the individual prescription items of a prescription order are displayed. The person may then visually inspect the items in the tray 80, may scan barcodes on labels of the items, may match a displayed image of a particular medication with a filled order, etc. After verifying the items for a prescription order, the person may proceed to a subsequent process such as forwarding the prescription order to a patient or healthcare facility, receiving payment for the order, communicating verification information with a PIS, etc.

Many variations in a workflow method are envisaged and it is intended that the invention be adaptable for order filling that includes any type of computer network and any type of computer, such as computers integrated with other aspects of a pharmacy, including those responsive to relative movements of a technician. In addition, the invention may incorporate additional writing of information to RFID tags and other media for effecting additional control of prescription order processing. For example, a system may be structured for using an RFID antenna to store updated filling information in an RFID tag 81.

While the principles of the invention have been shown and described in connection with specific embodiments, it is to be understood that such embodiments are by way of example and are not limiting.

What is claimed is:

1. A system for filling a prescription order for a patient comprising:
    a plurality of trays each having an RFID tag for storing a unique identifier corresponding to the prescription order;
    a plurality of workstations operatively linked to one another, each workstation having a reader for detecting the unique identifier in one of the plurality of trays and a computer, wherein the computer of each workstation is configured to organize individual prescription items in the prescription order in response to the detecting of the unique identifier and to display a profile of at least one unfilled prescription item for the corresponding prescription order in response to the detecting of the unique identifier;
    an input device structured for selecting the at least one unfilled individual prescription item for fulfillment;
    a printer operative for printing a label containing a barcode identifying the at least one unfilled prescription item; and
    a barcode reader for reading the barcode and determining from the barcode information whether the prescription item identified by the barcode matches a prescription item of the prescription order identified by the unique identifier.

2. The system of claim 1 wherein the computer of each workstation is configured to display the profile only while the reader is detecting the unique identifier.

3. The system of claim 1 wherein the unfilled prescription item selected for fulfillment is placed in a queue.

4. The system of claim 1 wherein the computer of each workstation is configured to generate a filling sequence for individual unfilled prescription items.

5. The system of claim 4 wherein the filling sequence is generated to minimize a cost function.

6. The system of claim 1 wherein the organization of the individual prescription items in the prescription order is based on determining which of the individual prescription items may be filled at a workstation of the plurality of workstations where the unique identifier is being detected.

7. The system of claim 1 wherein the display of the profile includes text information, medication image information, and a graphical user interface (GUI) symbol representing a respective storage location for the at least one unfilled prescription item.

8. The system of claim 1 wherein the computer of each workstation is configured to trigger automated dispensing of at least one of the unfilled prescription items based upon the detection of the unique identifier.

9. The system of claim 4 wherein:
at least one workstation includes a touchscreen;
the profile is displayed on the touchscreen, and the display includes graphical user interface (GUI) symbols representing the at least one unfilled prescription item, the display based on the filling sequence; and
the computer of the workstation is configured so that pressing a predetermined location on the touchscreen initiates an automated filling of one of the at least one unfilled prescription items of the profile.

10. The system of claim 9 wherein the barcode reader is operative to read a barcode printed on the label; and
wherein the computer of each workstation is configured to translate the barcode into verification information, and to determine from the verification information whether the at least one unfilled prescription item corresponds to the prescription order.

11. The system of claim 1 wherein the input device is selected from a touchscreen, a keyboard, a mouse or any combination thereof.

12. A system comprising:
a tray having an RFID tag containing a unique identifier;
an automated medication dispensing machine structured for dispensing individual medication amounts;
a workstation adapted for receiving the tray, the workstation including a computer operatively linked to the automated medication dispensing machine;
a reader operatively linked with the computer for reading the unique identifier of the tray received by the workstation, wherein the computer is configured to access prescription order information associated with the unique identifier in response to the reading of the unique identifier by the reader and to send a control signal to the automated medication dispensing machine to cause the dispensing of a prescription item of the prescription order associated with the unique identifier in response to the reading of the unique identifier by the reader; and
a printer operative for printing a label identifying the prescription order, wherein the label contains a barcode and the system further comprises a barcode reader for reading the barcode and determining from the barcode information whether the prescription order identified by the barcode matches the prescription order identified by the unique identifier.

13. A system for filling a prescription order for a patient comprising:
a plurality of trays each having an RFID tag for storing a unique identifier corresponding to the prescription order;
a plurality of workstations operatively linked to one another, each workstation having a reader for detecting the unique identifier in one of the plurality of trays and a computer;
wherein the computer of each workstation is configured to:
(a) display a profile of at least one prescription item for the corresponding prescription order in response to the detecting of the unique identifier; and (b) organize individual prescription items in the prescription order that corresponds to the unique patient identifier in response to the detecting of the unique identifier, wherein organizing includes listing of any unfilled individual prescription item in the prescription order and generating a filling sequence for unfilled individual prescription items; and
an input device structured for selecting the unfilled individual prescription item for fulfillment.

14. The system of claim 13 wherein the unfilled individual prescription item selected for fulfillment is placed in a queue.

15. The system of claim 13 wherein the filling sequence is generated to minimize a cost function.

16. The system of claim 13 wherein the organizing is based on determining which of the unfilled individual prescription items may be filled at a workstation of the plurality of workstations where the unique identifier is being detected.

17. A system for filling a prescription order for a patient comprising:
a plurality of trays each having an RFID tag for storing a unique identifier corresponding to the prescription order;
a plurality of workstations operatively linked to one another, each workstation having a reader for detecting the unique identifier in one of the plurality of trays and a computer; and
wherein the computer of each workstation is configured to trigger displaying of a profile of at least one prescription item for the corresponding prescription order in response to the detecting of the unique identifier, the displaying of the profile including presenting text information, medication image information, and a graphical user interface (GUI) symbol representing a respective storage location for the at least one prescription item.

18. A system for filling a prescription order for a patient comprising:
a plurality of trays each having an RFID tag for storing a unique identifier corresponding to the prescription order;
a plurality of workstations operatively linked to one another, each workstation having a touchscreen, a computer and a reader for detecting the unique identifier in one of the plurality of trays;
wherein the computer of each workstation is configured to trigger, in response to the detecting of the unique identifier: (a) displaying of a profile of at least one prescription item for the corresponding prescription order, the displaying of the profile including presenting on the touchscreen, based on a filling sequence, graphical user interface (GUI) symbols representing each of the at least one prescription items; and (b) organizing of individual prescription items in the prescription order that corresponds to the unique patient identifier, including generating the filling sequence for the at least one prescription item; and
wherein the computer of each workstation is configured so that pressing a predetermined location on the touchscreen initiates an automated filling of the at least one prescription item.

19. The system of claim 18 wherein the workstation includes a printer and the computer of each workstation is configured so that pressing of one of the GUI symbols initiates printing of a label by the printer for the corresponding prescription item.

20. The system of claim 19 further comprising a barcode reader operative to read a barcode printed on the label,
wherein the computer of each workstation is configured for translating the barcode into verification information, and for determining from the verification information whether the at least one prescription item corresponds to the prescription order.

21. A system for filling a prescription order for a patient comprising:
- a plurality of trays each having an RFID tag for storing a unique identifier corresponding to the prescription order; and
- a plurality of workstations operatively linked to one another, each workstation having: a touchscreen, a computer, a reader for detecting the unique identifier in one of the plurality of trays, and a printer,
- wherein the computer of each workstation is configured to trigger, in response to the detecting of the unique identifier: (a) displaying a profile of at least one prescription item for the corresponding prescription order, including presenting on the touchscreen, based on a filling sequence, graphical user interface (GUI) symbols representing each of the at least one prescription items; and (b) organizing of individual prescription items in the prescription order that corresponds to the unique identifier, including generating the filling sequence for the at least one prescription item; and
- wherein the computer of each workstation is configured so that pressing of one of the GUI symbols initiates printing of a label by the printer for the corresponding prescription item.

22. The system of claim 21 further comprising a barcode reader operative to read a barcode printed on the label,
- wherein the computer of each workstation is configured for translating the barcode into verification information, and for determining from the verification information whether the at least one prescription item corresponds to the prescription order.

23. A system for filling a prescription order for a patient comprising:
- a plurality of trays each having an RFID tag for storing a unique identifier corresponding to the prescription order;
- a plurality of workstations operatively linked to one another, each workstation having a touchscreen, a computer, a reader for detecting the unique identifier in one of the plurality of trays, a printer, and a barcode reader operative to read a barcode printed on the label;
- wherein the computer of each workstation is configured to trigger, in response to the detecting of the unique identifier: (a) displaying of a profile of at least one prescription item for the corresponding prescription order, including presenting on the touchscreen, based on a filling sequence, graphical user interface (GUI) symbols representing each of the at least one prescription items; and (b) organizing of individual prescription items in the prescription order that corresponds to the unique identifier, including generating the filling sequence for the at least one prescription item; and
- wherein the computer of each workstation is configured so that pressing one of the corresponding one of the GUI symbols initiates printing of a label including the barcode by the printer for the corresponding individual prescription item and the computer of each workstation is configured for translating barcode into verification information, and for determining from the verification information whether the at least one prescription item corresponds to a pending portion of the prescription order.

24. A system for filling a prescription order for a patient comprising:
- a plurality of trays each having an RFID tag for storing a unique identifier corresponding to the prescription order;
- a plurality of workstations operatively linked to one another, each workstation having a reader for detecting the unique identifier in one of the plurality of trays and a computer, wherein the computer is configured to trigger displaying of a profile of at least one prescription item for the corresponding prescription order including a listing of at least one unfilled individual prescription item in the prescription order in response to the detecting of the unique identifier;
- an input device structured for selecting the unfilled individual prescription item for fulfillment;
- a printer operative for printing a label containing a barcode identifying the prescription item; and
- a barcode reader for reading the barcode and determining from the barcode information whether the prescription item identified by the barcode matches a prescription item of the prescription order identified by the unique identifier.

\* \* \* \* \*